United States Patent
Kim et al.

(10) Patent No.: US 11,657,499 B2
(45) Date of Patent: May 23, 2023

(54) METHOD AND APPARATUS FOR PREDICTING PULMONARY DISEASE USING FRACTAL DIMENSION VALUE

(71) Applicants: THE ASAN FOUNDATION, Seoul (KR); UNIVERSITY OF ULSAN FOUNDATION FOR INDUSTRY COOPERATION, Ulsan (KR)

(72) Inventors: Namkug Kim, Seoul (KR); Jeongeun Hwang, Seoul (KR); Joon Beom Seo, Seoul (KR); Sang Min Lee, Seoul (KR)

(73) Assignees: THE ASAN FOUNDATION, Seoul (KR); UNIVERSITY OF ULSAN FOUNDATION FOR INDUSTRY COOPERATION, Ulsan (KR)

(*) Notice: Subject to any disclaimer, the term of this patent is extended or adjusted under 35 U.S.C. 154(b) by 367 days.

(21) Appl. No.: 16/934,103

(22) Filed: Jul. 21, 2020

(65) Prior Publication Data
US 2020/0349702 A1 Nov. 5, 2020

Related U.S. Application Data

(63) Continuation of application No. PCT/KR2019/000921, filed on Jan. 22, 2019.

(30) Foreign Application Priority Data

Jan. 22, 2018 (KR) .................. 10-2018-0007721

(51) Int. Cl.
*G06T 7/00* (2017.01)
*G06T 7/11* (2017.01)
(Continued)

(52) U.S. Cl.
CPC ............ *G06T 7/0012* (2013.01); *A61B 6/032* (2013.01); *A61B 6/50* (2013.01); *G06N 3/04* (2013.01);
(Continued)

(58) Field of Classification Search
CPC ......... G06T 7/0012; G06T 7/11; G06T 7/174; G06T 2207/10081; G06T 2207/20081;
(Continued)

(56) References Cited

U.S. PATENT DOCUMENTS

| | | | | |
|---|---|---|---|---|
| 2003/0103665 A1* | 6/2003 | Uppaluri | ............... | G06T 7/0012 382/173 |
| 2008/0269592 A1* | 10/2008 | Kuth | ..................... | A61B 5/411 600/407 |
| 2012/0189176 A1* | 7/2012 | Giger | ..................... | G06T 19/20 382/128 |

FOREIGN PATENT DOCUMENTS

| | | |
|---|---|---|
| JP | 2000-011146 A | 1/2000 |
| JP | 2007-068993 A | 3/2007 |

(Continued)

OTHER PUBLICATIONS

International Search Report issued in PCT/KR2019/000921; dated Apr. 30, 2019.

*Primary Examiner* — Vu Le
*Assistant Examiner* — Winta Gebreslassie
(74) *Attorney, Agent, or Firm* — Studebaker & Brackett PC

(57) ABSTRACT

A method for predicting a pulmonary disease includes acquiring a three-dimensional computed tomography (CT) image from two-dimensional CT images, each of which captures a respective body position of a first patient, dividing the three-dimensional CT image into a plurality of regions to obtain region-based three-dimensional CT images configured to be used for fractal analysis, calculating a region-based fractal dimension value indicating a fractal complexity of a respective region-based three-dimensional CT image among the generated region-based three-dimensional computed tomography images, adding additional information to the region-based fractal dimension value to generate high-
(Continued)

dimensional data, and generating status information of the first patient based on the complexity of the generated high-dimensional data.

13 Claims, 8 Drawing Sheets

(51) Int. Cl.
    *G06T 7/174*     (2017.01)
    *G16H 30/20*     (2018.01)
    *A61B 6/03*     (2006.01)
    *A61B 6/00*     (2006.01)
    *G06N 3/04*     (2023.01)
    *G06N 3/08*     (2023.01)

(52) U.S. Cl.
    CPC .................. *G06N 3/08* (2013.01); *G06T 7/11* (2017.01); *G06T 7/174* (2017.01); *G16H 30/20* (2018.01); *G06T 2207/10081* (2013.01); *G06T 2207/20081* (2013.01); *G06T 2207/30061* (2013.01)

(58) Field of Classification Search
    CPC .......... G06T 2207/30061; G16H 30/20; A61B 6/032; A61B 6/50; G06N 3/04; G06N 3/08
    See application file for complete search history.

(56) References Cited

FOREIGN PATENT DOCUMENTS

| | | | |
|---|---|---|---|
| JP | 6326264 B2 | * | 5/2018 |
| KR | 10-2015-0074304 A | | 7/2015 |
| KR | 10-2017-0046104 A | | 4/2017 |
| KR | 10-2017-0071009 A | | 6/2017 |
| KR | 10-2017-0096088 A | | 8/2017 |

* cited by examiner

METHOD AND APPARATUS FOR PREDICTING PULMONARY DISEASE USING FRACTAL DIMENSION VALUE

CROSS-REFERENCE TO RELATED APPLICATIONS

The present application is a continuation of International Patent Application No. PCT/KR2019/000921, filed on Jan. 22, 2019, which is based upon and claims the benefit of priority to Korean Patent Application No. 10-2018-0007721, filed on Jan. 22, 2018. The disclosures of the above-listed applications are hereby incorporated by reference herein in their entirety.

BACKGROUND

Embodiments of the inventive concept described herein relate to a method and an apparatus for predicting a pulmonary disease using a fractal dimension value.

A chronic obstructive pulmonary disease (COPD) is a respiratory disease in which a harmful gas or microparticles entering a lung causes coughing or sputum, in severe cases, dyspnea, and abnormal inflammation in the lung, thereby to gradually restrict airflow and to cause a lung function to deteriorate and to cause dyspnea. The COPD includes emphysema and chronic bronchitis.

A phenomenon that when an elderly person who smokes move more than a certain amount, that elderly person gets a short of breath and would have coughing and sputum. This symptom is commonly referred to as "cough asthma." This "cough asthma" could be one example of the COPD.

The most common cause of the COPD is smoking. Other factors, such as air pollution and genetics, also have a smaller impact thereon. In developing countries, improper ventilation of smoke from fire for cooking or heating is a main cause of air pollution.

Prolonged exposure to the above factors may cause inflammatory reactions in the lungs, thereby narrowing a small airway and causing emphysema in which a lung tissue is destroyed. When the airflow measured via a lung function test is poor, the COPD could be diagnosed.

A field of pulmonary disease medicine is investing a lot of effort in finding a prognosis prediction model to predict various pulmonary diseases including cancer. However, most conventional pulmonary disease prediction models do not reflect image data at all, or are based only on two-dimensional images. Thus, the most conventional pulmonary disease prediction models have reliability and accuracy considered to be somewhat insufficient to be widely used in a clinical field for the purpose of predicting a progress of the pulmonary disease.

Moreover, the most conventional pulmonary disease prediction models predict a progress of the pulmonary disease based on clinical results from the United States. In this regard, the prediction accuracy in other countries is relatively low.

SUMMARY

Embodiments of the inventive concept provide a method and an apparatus for predicting a pulmonary disease using a fractal dimension value.

The purpose of the present disclosure is not limited thereto. Other purposes as not mentioned will be clearly understood by those skilled in the art from following descriptions.

According to an exemplary embodiment, a method for predicting a pulmonary disease includes acquiring, by an acquisitor of a pulmonary disease prediction apparatus, a three-dimensional computed tomography (CT) image from two-dimensional CT images, each of which captures a respective body position of a first patient, dividing, by a controller of the pulmonary disease prediction apparatus, the three-dimensional CT image into a plurality of regions, to generate region-based three-dimensional CT images configured to be used for fractal analysis, calculating, by the controller, a region-based fractal dimension value indicating a fractal complexity of a respective region-based three-dimensional CT image among the generated region-based three-dimensional CT images, adding, by the controller, additional information to the calculated region-based fractal dimension value to generate high-dimensional data, and generating, by the controller, status information of the first patient based on the complexity of the generated high-dimensional data.

According to an exemplary embodiment, a pulmonary disease prediction apparatus includes a processor, and a memory storing at least one instruction executable by the processor, wherein the at least one instruction is executed by the processor to acquire, through an acquisitor of the pulmonary disease prediction apparatus, a three-dimensional computed tomography (CT) image from two-dimensional CT images, each of which captures a respective body position of a first patient, divide the three-dimensional CT image into a plurality of regions, to generate region-based three-dimensional CT images configured to be used for fractal analysis, calculate a region-based fractal dimension value indicating a fractal complexity of a respective region-based three-dimensional CT image among the generated region-based three-dimensional CT images, add additional information to the calculated region-based fractal dimension value to generate high-dimensional data, and generate status information of the first patient based on the complexity of the generated high-dimensional data.

According to an exemplary embodiment, a non-transitory computer-readable recording medium storing a program for executing the method for predicting the pulmonary disease in combination with a pulmonary disease prediction apparatus as hardware.

According to an exemplary embodiment, a pulmonary disease prediction system comprising: a controller configured to generate prognosis prediction information of a second patient based on a prognosis prediction model, wherein the prognosis prediction model is generated by the controller that applies a machine learning algorithm to high-dimensional data of at least one first patient, wherein the high-dimensional data is generated by the controller that adds additional information into a region-based fractal dimension value, wherein the region-based fractal dimension value indicates a fractal complexity of a region-based three-dimensional computed tomography (CT) image, wherein the region-based three-dimensional CT image is generated by the controller that divides a three-dimensional CT image, and wherein the three-dimensional CT image is obtained based on two-dimensional CT images, each of which captures a respective body position of each of the first patient.

Other features of the present disclosure are included in the detailed description and drawings.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
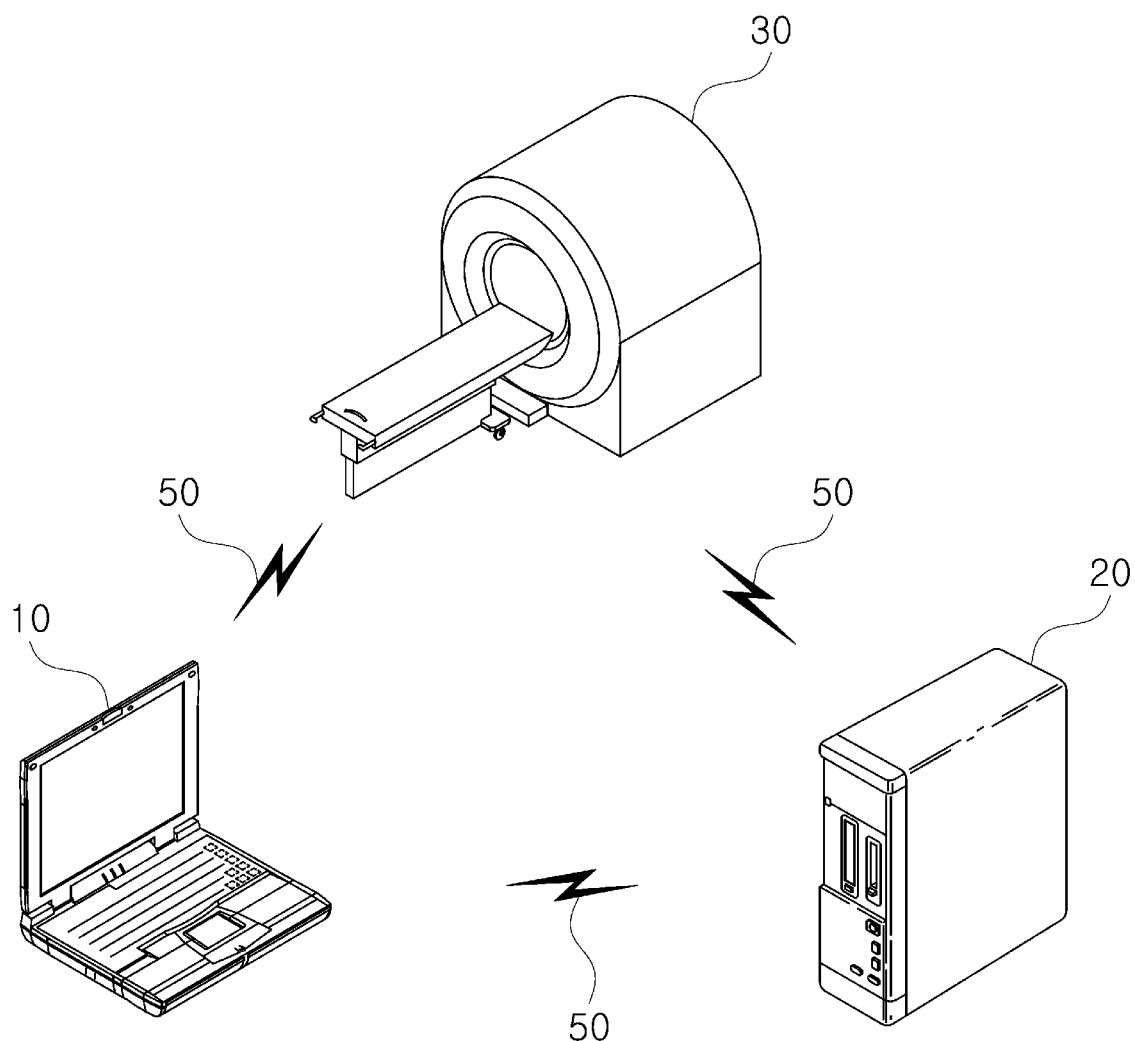
FIG. 1 is a conceptual diagram showing apparatuses for performing a method for predicting a pulmonary disease according to some embodiments of the present disclosure.

Advantages and features of the inventive concept, and methods of achieving them will become apparent with reference to embodiments described below in detail in conjunction with the accompanying drawings. However, the inventive concept is not limited to the embodiments disclosed below, but may be implemented in various forms. The present embodiments are provided to merely complete the disclosure of the inventive concept, and to inform merely fully those skilled in the art of the inventive concept of the scope of the inventive concept. The inventive concept is only defined by the scope of the claims.

The terminology used herein is for the purpose of describing the embodiments only and is not intended to limit the inventive concept. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. Like reference numerals refer to like elements throughout the disclosure. As used herein, the term "and/or" includes any and all combinations of one or more of the associated listed items. Although terms "first", "second", etc. are used to describe various components, it goes without saying that the components are not limited by these terms. These terms are only used to distinguish one component from another component. Therefore, it goes without saying that a first component as mentioned below may be a second component within a technical idea of the inventive concept.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Spatially relative terms "below", "beneath", "lower", "above", "upper", and the like may be used to easily illustrate a correlation between components as shown in the drawings. The spatially relative terms should be understood as terms including an orientation of a component varying in use or operation in addition to an orientation as shown in the drawings. For example, when a drawing is turned over, a first component described as "below" or "beneath" a second component may be placed "above" the second component. Accordingly, the exemplary term "below" may include both "below" and "above". A component may be oriented in a varying direction. Accordingly, the spatially relative terms may be interpreted according to the orientation.

Hereinafter, embodiments of the inventive concept will be described in detail with reference to the accompanying drawings.

FIG. 1 is a conceptual diagram showing apparatuses for providing a method for predicting a pulmonary disease according to some embodiments of the present disclosure.

Referring to FIG. 1, a pulmonary disease prediction system for providing a method for predicting a pulmonary disease state change of the inventive concept includes at least one of a user device 10, a server 20, and a pulmonary disease prediction apparatus 30. The user device 10, the server 20, and the pulmonary disease prediction apparatus 30 are connected to each other over a network 50. As used herein, in some embodiments, the pulmonary disease measured by the pulmonary disease prediction apparatus 30 is a chronic obstructive pulmonary disease (COPD), but in some other embodiments, it is not limited thereto. In some embodiments, the pulmonary disease prediction apparatus 30 is applied to a lung cancer using a different algorithm.

Examples of the user device 10 of the present disclosure include a desktop computer, a laptop computer, a tablet PC, a wireless phone, a mobile phone, a smart phone, a mobile station (MS), a machine-type communication (MTC) device, a M2M (machine-to-machine) device, a D2D (device-to-device) device, user equipment (UE), a wireless device, a wireless terminal (WT), an access terminal (AT), a wireless transmit/receive unit (WTRU), a subscriber station (SS), a subscriber unit (SU), a user terminal (UT), PMP (portable multimedia player), a personal portable terminal (PDA) with wireless communication function, a portable game device with wireless communication function, a navigation device, a digital camera, a DMB (digital multimedia broadcasting) player, a digital audio recorder, a digital audio player, a digital picture recorder, a digital picture player, a digital video recorder, a digital video player, a music storage and playback home appliance with wireless communication function, an internet home appliance capable of wireless internet access and browsing, and portable units or terminals incorporating combinations of the above functions. However, the present disclosure is not limited thereto.

Examples of the server 20 of the present disclosure include a cloud server, an IMS (IP multimedia subsystem) server, a telephony application server, a IM (instant messaging) server, a MGCF (media gateway control function) server, a MSG (messaging gateway) server, a CSCF (call session control function) server. In some embodiments, the server 20 is implemented as an apparatus that refers to an object that transmits and receives data, such as a PC (Personal Computer), a notebook computer, and a tablet PC.

The network 50 of the present disclosure refers to a data communication network for data transmission and reception between the user device 10, the server 20, and the pulmonary disease prediction apparatus 30. A type thereof is not particularly limited.

Examples of the network 50 of the present disclosure include an IP (Internet Protocol) network providing a large data transmission and reception service through the Internet protocol (IP), or include an all IP network that integrates different IP networks.

Herein, in some embodiments, the communication between the user device 10, the server 20, and the pulmonary disease prediction apparatus 30 is established over at least one selected from wireless Internet such as Wi-Fi wireless fidelity, portable Internet such as 802.11x (e.g., 802.11a, 802.11b, 802.11g, 802.11n, 802.11ac), WiBro (wireless broadband internet) or WiMAX (world interoperability for microwave access), a 2G (Second Generation) mobile communication network, such as GSM (global system for mobile communication) or CDMA (code division multiple access), a 3G (Third Generation) mobile communication network, such as WCDMA (wideband code division multiple access) or CDMA2000, a 3.5 G mobile communication network, such as HSDPA (high speed downlink packet access) or HSUPA (high speed uplink packet access), a 4G (Fourth Generation) mobile communication network, such as LTE (long term evolution network) or LTE-Advanced (LTE-A) network, 5G (Fifth Generation) mobile communication network, UWB (Ultra-Wide Band), Bluetooth, Zigbee, a satellite communication network, and combinations thereof.

Figure 2:
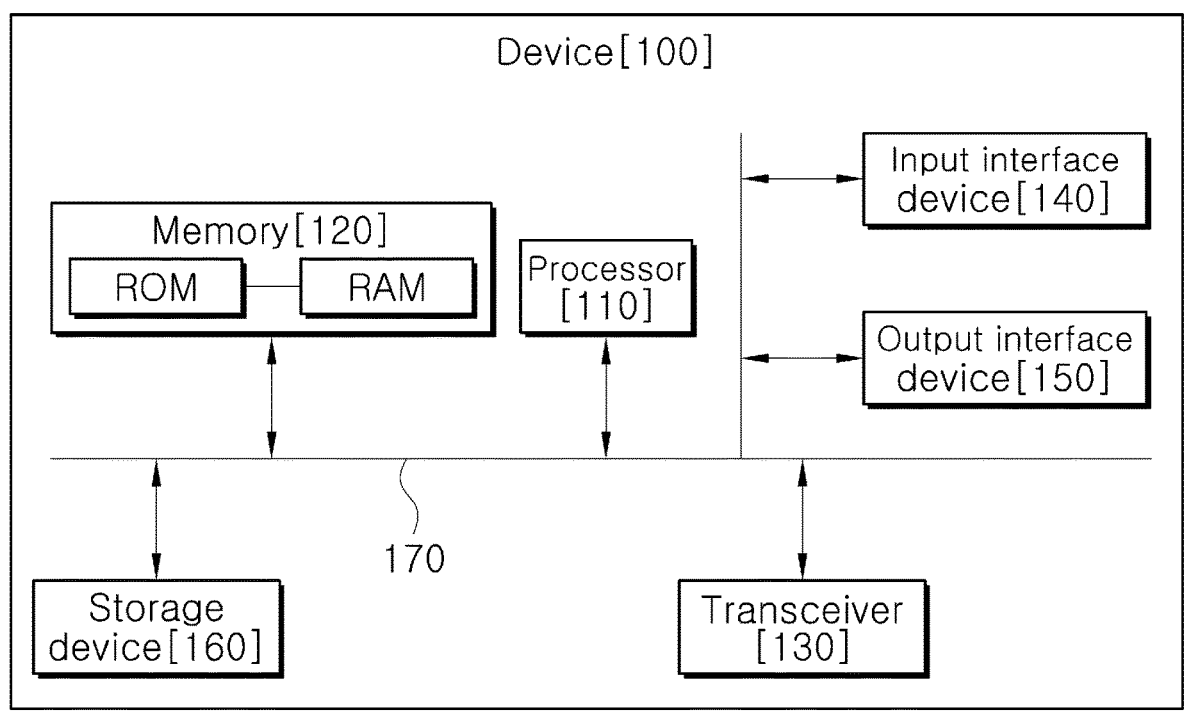
FIG. 2 is a block diagram showing a configuration of a device configured to perform a method for predicting a pulmonary disease according to some embodiments of the present disclosure.

FIG. 2 is a block diagram showing a configuration of a device configured to perform a method for predicting a pulmonary disease according to some embodiments of the present disclosure.

Referring to FIG. 2, a device 100 in some embodiments is the user device 10, and the device 100 in some other embodiments is the server 20. That is, the device 100 is a device configured to perform a method for predicting a pulmonary disease according to some embodiments of the present disclosure. The device 100 in some embodiments includes at least one processor 110, a memory 120, and a transceiver 130 connected to the network 50 to perform communication. Moreover, the device 100 in some embodiments further includes an input interface device 140, an output interface device 150, a storage device 160, and the like. The components included in the device 100 in some embodiments is connected to each other via a bus 170 and communicates with each other.

The output interface device 150 in some embodiments is a display. In these embodiments, the display displays and outputs information processed by the user device 10. Specifically, the display in some embodiments displays access information required for wired/wireless connection, advertisement information, or access information re-entry request command using a UI (user interface) or a GUI (graphic user interface).

Further, the display in some embodiments includes at least one of a liquid crystal display, a thin film transistor-liquid crystal display, an organic light-emitting diode, a flexible display, and a 3D display. The display in some embodiments includes two or more thereof depending on implementations. For example, an external display and an internal display in some embodiments is simultaneously provided in the user device 10.

The processor 110 in some embodiments executes a program command stored in at least one of the memory 120 and the storage device 160. The processor 110 in some embodiments includes a central processing unit (CPU), a graphics processing unit (GPU), or a dedicated processor in which methods according to some embodiments of the present disclosure are performed. Each of the memory 120 and the storage device 160 in some embodiments is embodied as at least one of volatile storage medium and non-volatile storage medium (i.e., non-transitory storage medium). For example, the memory 120 in some embodiments includes at least one of a read only memory (ROM) and a random access memory (RAM).

Figure 3:
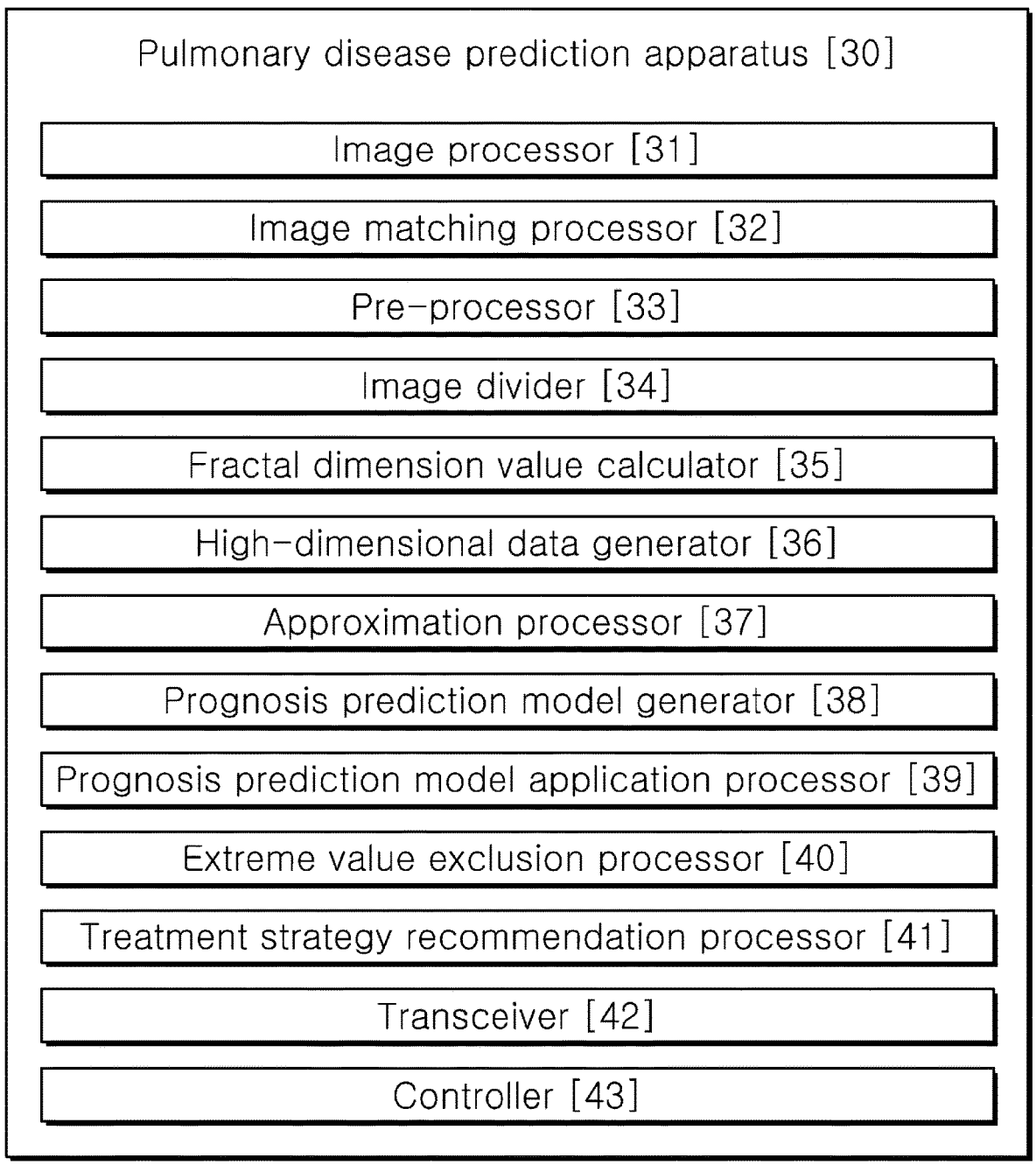
FIG. 3 is a block diagram showing a configuration of a pulmonary disease prediction apparatus according to some embodiments of the present disclosure.

FIG. 3 is a block diagram showing a configuration of a pulmonary disease prediction apparatus according to some embodiments of the present disclosure.

Referring to FIG. 3, the pulmonary disease prediction apparatus 30 according to one embodiment of the inventive concept includes at least one of an imaging processor 31, an image matching processor 32, a pre-processor 33, an image divider 34, a fractal dimension value calculator 35, a high-dimensional data generator 36, an approximation processor 37, a prognosis prediction model generator 38, a prognosis prediction model application processor 39, an extreme value exclusion processor 40, a treatment strategy recommendation processor 41, a transceiver 42, and a controller 43.

The imaging processor 31 in some embodiments images two-dimensional computed tomography (CT) images captured for body positions of a first patient. Alternatively, the imaging processor 31 in some embodiments utilize two-dimensional CT images received from an external apparatus. In these embodiments, the CT image in some embodiments includes images captured by a CT apparatus while moving along a human body for a specific time.

The image matching processor 32 acquires a three-dimensional CT image based on the two-dimensional CT images, each of which captures a respective position of a patient. Specifically, the image matching processor 32 in some embodiments stacks a plurality of the two-dimensional CT images that capture body positions of a patient, thereby to acquire the three-dimensional CT image.

Moreover, the image matching processor 32 in some embodiments matches the three-dimensional CT image based on a standard lung image. In these embodiments, the standard lung image refers to a standard lung shape defined based on physical conditions, such as a height, a weight, and a gender.

The pre-processor 33 in some embodiments transforms the three-dimensional CT image into data configured to be processed for image analysis. Specifically, the pre-processor 33 in some embodiments classifies data on a pixel or voxel basis.

The pre-processor 33 in some embodiments adjusts an image intensity of the captured image.

The image divider 34 in some embodiments divides the three-dimensional CT image into regions for fractal analysis. Specifically, the image divider 34 in some embodiments divides the captured three-dimensional CT image of the lung into a plurality of regions. This is because a scheme for predicting a pulmonary disease varies based on a position of a lung.

The fractal dimension value calculator 35 in some embodiments calculates a fractal dimension value indicating a fractal complexity of the region-based three-dimensional CT image in which the three-dimensional CT image are divided into a plurality of regions. A process of calculating the fractal dimension value using a box-count scheme, meaning of the fractal complexity, and a method of calculating a fractal dimension are described in detail below, in relation to FIG. 7.

The high-dimensional data generator 36 in some embodiments adds additional information into a region-based fractal dimension value, that is, a fractal dimension value for each region, thereby to generate high-dimensional data. In these embodiments, the additional information includes information about a density of a lung in an inhalation or exhalation state of a first patient. In these embodiments, the high-dimensional data refers to information including the fractal dimension value having a non-integer dimension and the additional information added thereto. The high-dimensional data in some embodiments includes information about the fractal dimension value according to various situations (e.g., whether a current state is the inhalation or exhalation state, or whether contrast media has been administered to the first patient, etc.).

In these embodiments, the non-integer dimension refers to a dimension such as '2.37', '1.78', and '2.65' that is not an integer.

Specifically, the additional information in some embodiments means information that affects the three-dimensional CT image in addition to the first patient's body information. The approximation processor 37 in some embodiments approximates the high-dimensional data into a linear value.

The prognosis prediction model generator 38 in some embodiments applies a machine learning algorithm to the high-dimensional data acquired from the first patient to generate a prognosis prediction model that predicts a status change in a second patient. In these embodiments, an accuracy of the machine learning algorithm using the high-dimensional data would be improved when the first patient belongs to an unspecified number of persons rather than a specific person.

The prognosis prediction model in some embodiments means a model for predicting how long the first patient further lives based on the pulmonary disease image of the first patient. In these embodiments, the pulmonary disease image and data on a survival probability of a patient with the pulmonary disease image is pre-acquired from an external apparatus.

The prognosis prediction model application processor 39 in some embodiments applies the three-dimensional CT image acquired from the second patient to the prognosis prediction model to generate prognosis prediction information of the second patient. In these embodiments, the first patient is a patient distinct from the second patient.

The extreme value exclusion processor 40 in some embodiments excludes an extreme value that occurs in a machine learning algorithm step. Specifically, the extreme value exclusion processor 40 in some embodiments excludes a high-dimensional data value having a measurement value or a ratio above a predetermined criterion or below a predetermined criterion occurring in a process of the machine learning algorithm. This is to prevent distortion of a machine learning result due to some extreme exceptional values.

The treatment strategy recommendation processor 41 in some embodiments derives at least one of a treatment timing and a treatment strategy based on the prognosis prediction information of the second patient acquired through the prognosis prediction model application processor 39.

The transceiver 42 in some embodiments externally receives the two-dimensional CT images. In addition, the transceiver 42 in some embodiments transmits at least one of the treatment timing and the treatment strategy to the user device 10.

The controller 43 in some embodiments controls an overall operation of at least one of the imaging processor 31, the image matching processor 32, the pre-processor 33, the image divider 34, the fractal dimension value calculator 35, the high-dimensional data generator 36, the approximation processor 37, the prognosis prediction model generator 38, the prognosis prediction model application processor 39, the extreme value exclusion processor 40, the treatment strategy recommendation processor 41, and the transceiver 42 of the pulmonary disease prediction apparatus 30.

Moreover, the pulmonary disease prediction apparatus 30 in some embodiments further includes an acquisitor, which is configured to acquire the captured image from an external apparatus or directly capture an image.

Figure 4:
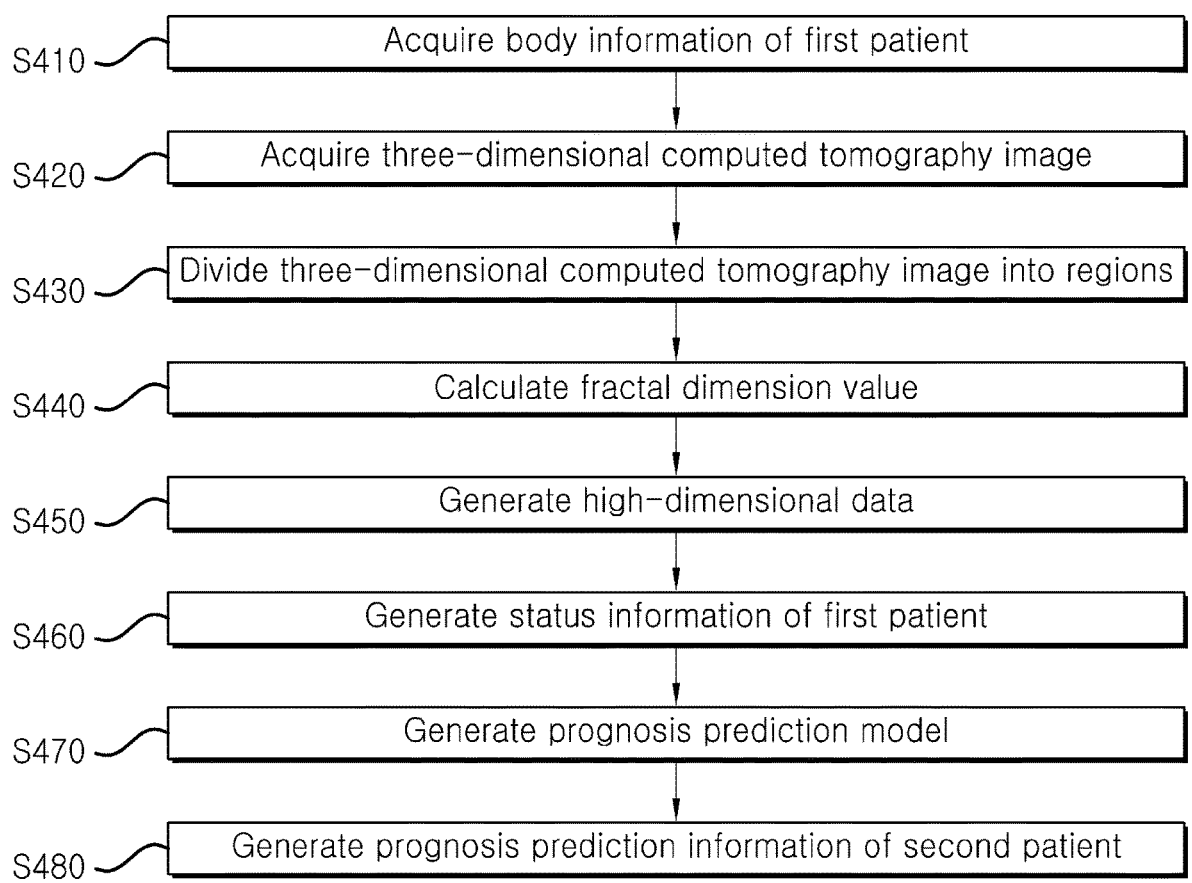
FIG. 4 is a flowchart illustrating a method for predicting a pulmonary disease according to some embodiments of the present disclosure.

FIG. 4 is a flowchart showing a method for predicting a pulmonary disease according to some embodiments of the present disclosure.

Referring to FIG. 4, the pulmonary disease prediction apparatus 30 in some embodiments acquires body information of the first patient (S410). In these embodiments, the body information includes information that specifies a specific patient, among information that affects the three-dimensional CT image. For example, a height of a specific patient, a weight thereof, and whether he/she has a respiratory disease may specify the specific patient are classified as the body information.

A reason why the body information is acquired is that a survival rate of each of a plurality of patients with similar pulmonary disease images varies based on the body information thereof.

The pulmonary disease prediction apparatus 30 in some embodiments acquires the three-dimensional CT image based on the two-dimensional CT images, each of which captures a respective body position of the first patient (S420). Specifically, the pulmonary disease prediction apparatus 30 in some embodiments stacks the plurality of two-dimensional CT images to acquire the three-dimensional CT image.

The pulmonary disease prediction apparatus 30 in some embodiments divides the three-dimensional CT image into regions (S430). The pulmonary disease prediction apparatus 30 in some embodiments divides the three-dimensional CT image into regions of the lung based on a predetermined rule. That is, the pulmonary disease prediction apparatus 30 in some embodiments divides the three-dimensional CT image into the regions to obtain region-based three-dimensional CT images.

The pulmonary disease prediction apparatus 30 in some embodiments calculates the fractal dimension value indicating the fractal complexity of each region-based three-dimensional CT images (S440).

The pulmonary disease prediction apparatus 30 in some embodiments adds the additional information into a region-based fractal dimension value to generate the high-dimensional data of the first patient (S450).

The pulmonary disease prediction apparatus 30 in some embodiments generates status information of the first patient based on the complexity of the high-dimensional data of the first patient (S460).

In some embodiments, the complexity of high-dimensional data is a value indicating a complexity level of the mentioned high-dimensional data.

Regarding the chronic pulmonary disease, in a 'healthy' state, a normal lung tissue is well preserved in a complex and delicate shape. In an 'unhealthy' state, the complex and delicate shape is lost due to the chronic pulmonary disease.

The lung cancer and the chronic pulmonary disease may have opposite phenomena to each other. For the lung cancer, it may be expected that the higher the shape complexity of a lesion area of the lung cancer, the worse the prognosis. To the contrary, it may be expected that the lower the shape complexity of the lesion site, the higher a treatment effect.

The pulmonary disease prediction apparatus 30 in some embodiments transmits the current state information of the first patient as generated to the user device 10. The user device 10 in some embodiments receives the status information of the first patient from the pulmonary disease prediction apparatus 30.

The user device 10 in some embodiments provides visual or auditory information about the status of the first patient.

Moreover, in some other embodiments, the pulmonary disease prediction apparatus 30 generates prognosis prediction information of the second patient based on the prognosis prediction model generated by applying the machine learning algorithm to the high-dimensional data. The pulmonary disease prediction apparatus 30 in those embodiments applies the machine learning algorithm to the high-dimension data to generate the prognosis prediction model that predicts the status change of the second patient. Alternatively, the prognosis prediction model that has already been generated is used by the pulmonary disease prediction apparatus 30.

Specifically, when the pulmonary disease prediction apparatus 30 generates the prognosis prediction model, the pulmonary disease prediction apparatus 30 in some embodiments applies the machine learning algorithm to the high-dimensional data to generate the prognosis prediction model that predicts the status change of the second patient (S470). The pulmonary disease prediction apparatus 30 in some embodiments further considers the body information of the first patient for the generation of the prognosis prediction model. Moreover, the pulmonary disease prediction apparatus 30 in some embodiments further considers the body information of the second patient for generation of prognosis prediction information of the second patient.

The pulmonary disease prediction apparatus 30 in some embodiments generates the prognosis prediction information of the second patient based on the prognosis prediction model (S480).

Figure 5:
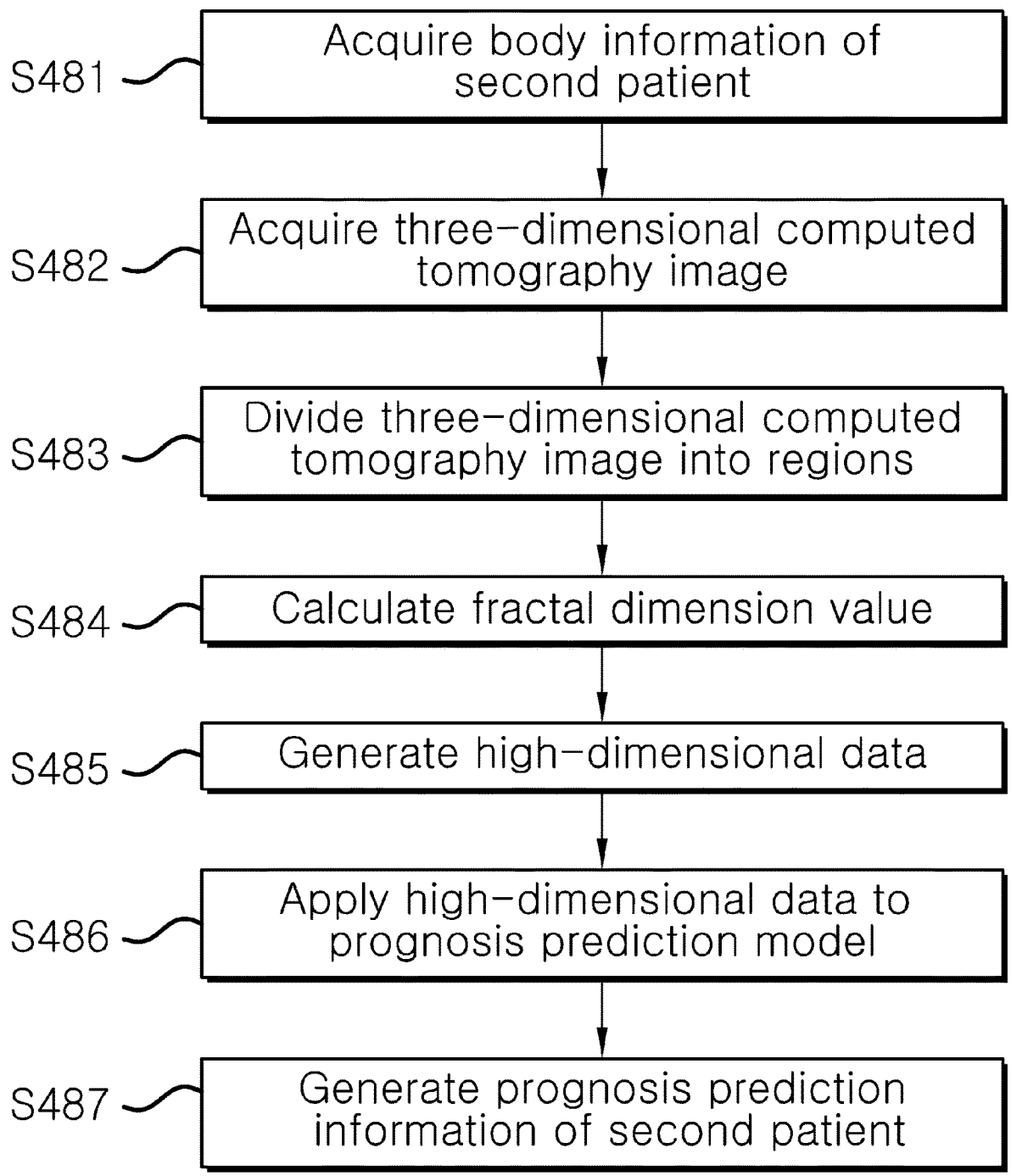
FIG. 5 is a flowchart showing a method for generating prognosis state prediction information of a second patient according to some embodiments of the present disclosure.

FIG. 5 is a flowchart showing a method of generating the prognosis state prediction information of the second patient according to some embodiments of the present disclosure.

Referring to FIG. 5, the pulmonary disease prediction apparatus 30 in some embodiments acquires the body information of the second patient (S481). In these embodiments, the body information includes information that is distinguished between patients, among information that affects the three-dimensional CT image.

For example, a patient's height, weight, and whether he/she has a respiratory disease are distinguished between the patients and thus are classified as the body information.

The pulmonary disease prediction apparatus 30 in some embodiments acquires the three-dimensional CT image based on the two-dimensional CT images captured for body positions of the second patient (S482). Specifically, the pulmonary disease prediction apparatus 30 in some embodiments stacks the plurality of the two-dimensional CT images captured based on body positions of the second patient to obtain the three-dimensional CT image.

The pulmonary disease prediction apparatus 30 in some embodiments divides the three-dimensional CT image into regions (S483). The pulmonary disease prediction apparatus 30 in some embodiments divides the three-dimensional CT image into regions of the lung on a predetermined rule.

The pulmonary disease prediction apparatus 30 in some embodiments calculates the fractal dimension value indicating the fractal complexity of the region-based three-dimensional CT image (S484).

The pulmonary disease prediction apparatus 30 in some embodiments adds the additional information to the region-based fractal dimension value to generate the high-dimensional data of the second patient (S485).

The pulmonary disease prediction apparatus 30 in some embodiments applies the high-dimensional data of the second patient to the generated prognosis prediction model (S486). The pulmonary disease prediction apparatus 30 in some embodiments generates the prognosis prediction information of the second patient based on the prognosis prediction model (S487).

The pulmonary disease prediction apparatus 30 in some embodiments transmits the prognosis prediction information of the second patient to the user device 10. The user device 10 in some embodiments receives the prognosis prediction information of the second patient from the pulmonary disease prediction apparatus 30.

The user device 10 in some embodiments provides visual or audible prognosis state prediction information of the second patient.

Figure 6:
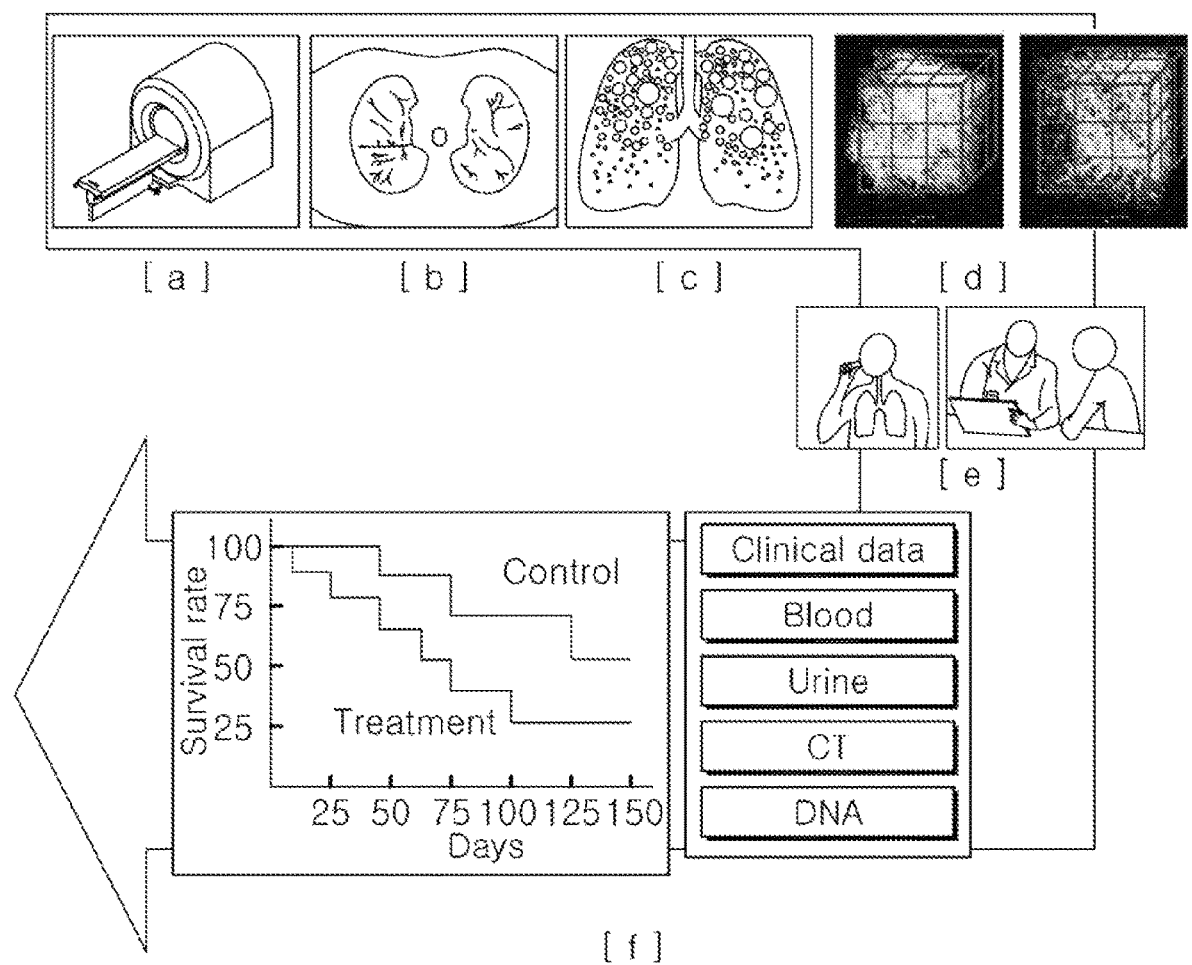
FIG. 6 is a conceptual diagram showing a method for predicting a pulmonary disease according to some embodiments of the present disclosure.

FIG. 6 is a conceptual diagram showing a method for predicting a pulmonary disease according to some embodiments of the present disclosure.

In FIG. 6, [a] of FIG. 6 shows a process of acquiring a lung image from a patient. [b] of FIG. 6 shows a process of processing the lung image obtained from the patient. [c] of FIG. 6 shows a process of automatically dividing a medical lung image acquired from the patient into regions. [d] of FIG. 6 shows a process of analyzing a high-dimensional fractal image.

[e] of FIG. 6 shows a process of collecting lung function test data, questionnaire data, and the like. In these embodiments, the questionnaire data refers to a diagnostic method in which questions are asked from the doctor's point of view, the patient's complaining symptoms are answered and the medical history of the patient's family is checked. [f] of FIG. 6 shows a process of generating a prognosis prediction model of a patient with pulmonary disease. In some embodiments, the processes shown in FIG. 6 are sequentially processed.

Figure 7:
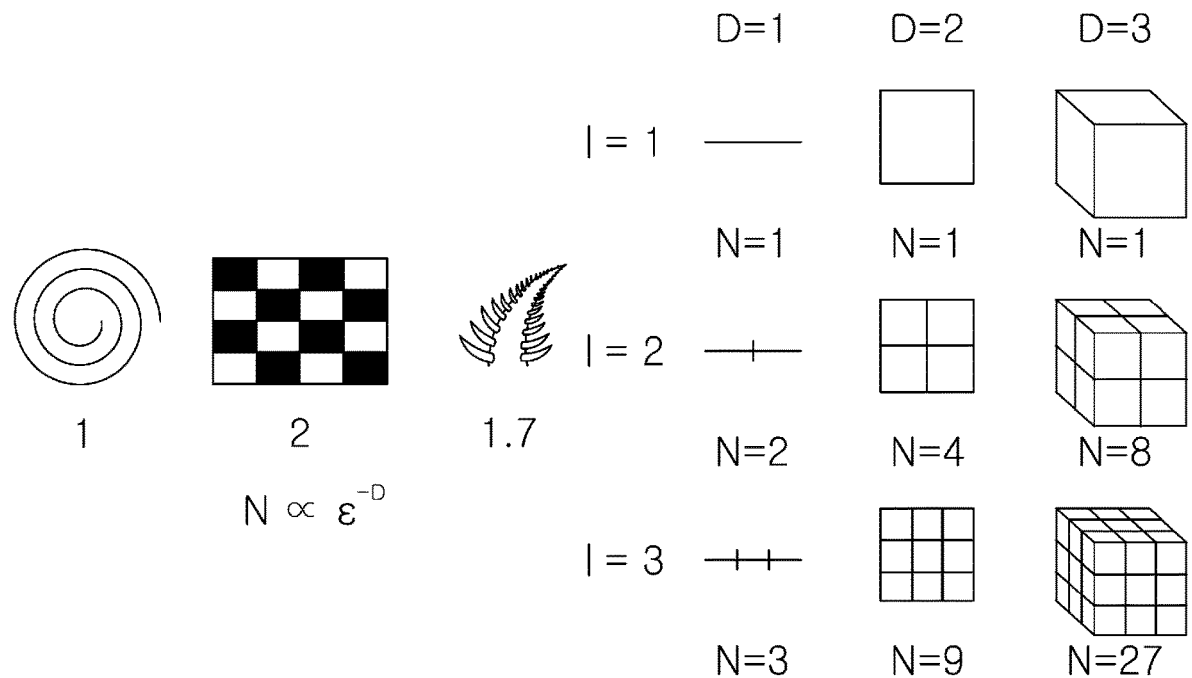
FIG. 7 is a conceptual diagram showing a process of deriving a fractal dimension according to some embodiments of the present disclosure.
Figure 7:
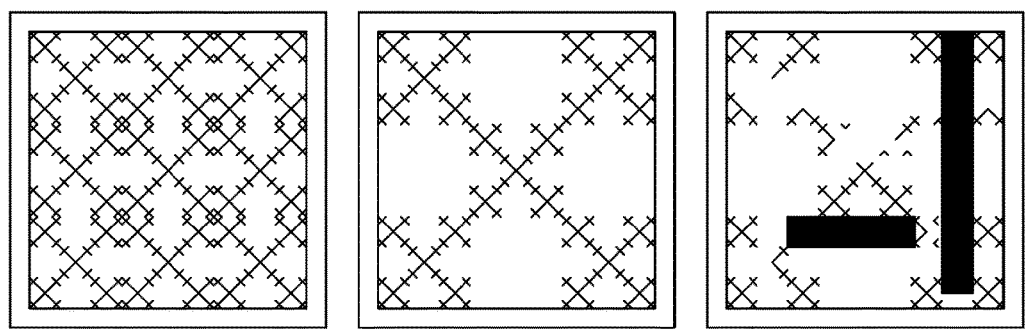

FIG. 7 is a conceptual diagram showing a process of deriving a fractal dimension according to some embodiments of the present disclosure.

Referring to FIG. 7, the fractal refers to a structure in which a simple structure is constantly repeated, thereby creating a complex and strange overall structure. The fractal has characteristics of 'self-similarity' and 'reclusiveness'. A fractal pattern is common in nature, such as a rias coastline, a tree branch, a frost growing on a window, and a mountain shape. The fractal pattern has been found in an animal blood vessel distribution pattern, life phenomena, especially, in a shape of living organs and tissues.

A fractal shape to which a fractal principle is applied is a complex shape that is generated via a simple self-repeating algorithm and has the non-integer dimension.

The fractal analysis refers to calculating the non-integer dimension of the fractional, that is, the fractal dimension value, as described above. Specifically, a box-counting scheme is used for the fractal analysis.

The box-counting scheme may be the most basic method for measuring the fractal dimension of a predefined shape. In this scheme, virtual boxes are created in various sizes and a power law is established between the number N of boxes required to cover a shape and a size £ of each of the boxes. An exponent D of a power function may be a box-counting fractal dimension of the shape.

In general, a size of the box-counting fractal dimension may represent space-filling property and geometric complexity. Specifically, the larger the fractal dimension, the more complex the shape. The lower the fractal dimension, the simpler the shape. That is, the larger the fractal dimension, the greater the 'fractal complexity'. The lower the fractal dimension, the lower the 'fractal complexity'.

The fractal analysis is robust to a noise common in an image captured in a non-uniform imaging condition, artifacts due to varying smoothing degrees, an image reconstruction condition, and different algorithms, and variations in enlargement-shrinkage ratio, X-ray brightness, resolution, etc. Thus, the fractal analysis may be advantageously in analyzing multi-center KOLD cohort medical images.

Most of published MATLAB or C source codes, application, etc. for measuring the box-counting fractal dimension are an algorithm which is applied to a two-dimensional image for measurement using a two-dimensional box. In the present disclosure, a box-counting fractal dimension analysis algorithm using a three-dimensional box for application to a three-dimensional image is created and used.

A box-counting fractal dimension analysis algorithm is commonly referred to as a method of gathering data for analyzing complex patterns by breaking a dataset, object, image, etc. into smaller and smaller pieces, typically "box"-shaped, and analyzing the pieces at each smaller scale. In box counting, computer based box counting algorithms have been applied to patterns in 1-, 2-, and 3-dimensional spaces. The technique is usually implemented in software for use on patterns extracted from digital media. The technique arose out of and is used in fractal analysis. It also has application in related fields such as lacunarity and multifractal analysis. See, e.g., Wikipedia, Box counting, https://en.wikipedia.org/wiki/Box_counting (URL included merely to provide written description).

Lacunarity A is an indicator of translational and rotational inhomogeneity. For calculating the lacunarity A, in a similar manner to the box-counting fractal dimension analysis, while moving along virtual boxes of various sizes £ move in a direction, the number of voxels in each box is measured, and the lacunarity A is expressed as a square of a coefficient of variation thereof.

Conventional algorithms providing a fractal dimension analysis function are targeted toward a two-dimensional image. For example, in Mishima research as a representative study of emphysema image fractal analysis, three slices are randomly sampled from upper, middle, and lower regions of the CT image of the lung and the sampled slices are applied to two-dimensional fractal analysis.

In addition to the research cases applied to the lung, the fractal analysis algorithms targeting general images are configured to work on the two-dimensional images. Intuitively, a soft tissue of the lung occupies a three-dimensional space, and CT image data is constructed in a three-dimensional manner. Thus, when measuring the fractal dimension D, it is desirable to measure the maximum D=3 or lower.

When performing the two-dimensional phase fractal analysis conventionally, only a maximum value of D=2 or lower may be measured as a fractal dimension value. When two-dimensional sampling is done in a well-designed way to have statistical representativeness, the fractal dimension as measured in this way may have the same tendency as that of values measured in a full-3D manner.

In many patterns or data sets, lacunarity is not readily perceivable or quantifiable, so computer-aided methods have been developed to calculate it. As a measurable quantity, lacunarity is often denoted in scientific literature by $\Lambda$ or $\lambda$. One well-known method of determining lacunarity for patterns extracted from digital images uses box counting, as mentioned above. Box counting algorithms look at a digital image from many levels of resolution to examine how certain features change with the size of the element used to inspect the image. Basically, the arrangement of pixels is measured using traditionally square (i.e., box-shaped) elements from an arbitrary set of sizes, conventionally denoted ES. For each c, the box is placed successively over the entire image, and each time it is laid down, the number of pixels that fall within the box is recorded. In standard box counting, the box for each c in E is placed as though it were part of a grid overlaid on the image so that the box does not overlap itself, but in sliding box algorithms the box is slid over the image so that it overlaps itself and the "Sliding Box Lacunarity" or SLac is calculated.

The data gathered for each c are manipulated to calculate lacunarity. One measure, denoted here as $\lambda_e$, is found from the coefficient of variation (CV), calculated as the standard deviation ($\sigma$) divided by the mean ($\mu$), for pixels per box. Because the way an image is sampled will depend on the arbitrary starting location, for any image sampled at any c there will be some number (G) of possible orientations, each denoted here by g, that the data can be gathered over, which can have varying effects on the measured distribution of pixels. Equation 1, below, shows the basic method of calculating $\lambda_{e,g}$, as also shown in FIG. 7. See, e.g., Wikipedia, Lacunarity, http://en.wikipedia.org/wiki/Lacunarity#Box_counting_lacunarity (URL included merely to provide written description).

$$\lambda_{\varepsilon,g} = (CV_{\varepsilon,g})^2 = \left(\frac{\sigma_{\varepsilon,g}}{\mu_{\varepsilon,g}}\right)^2$$

Figure 8A:
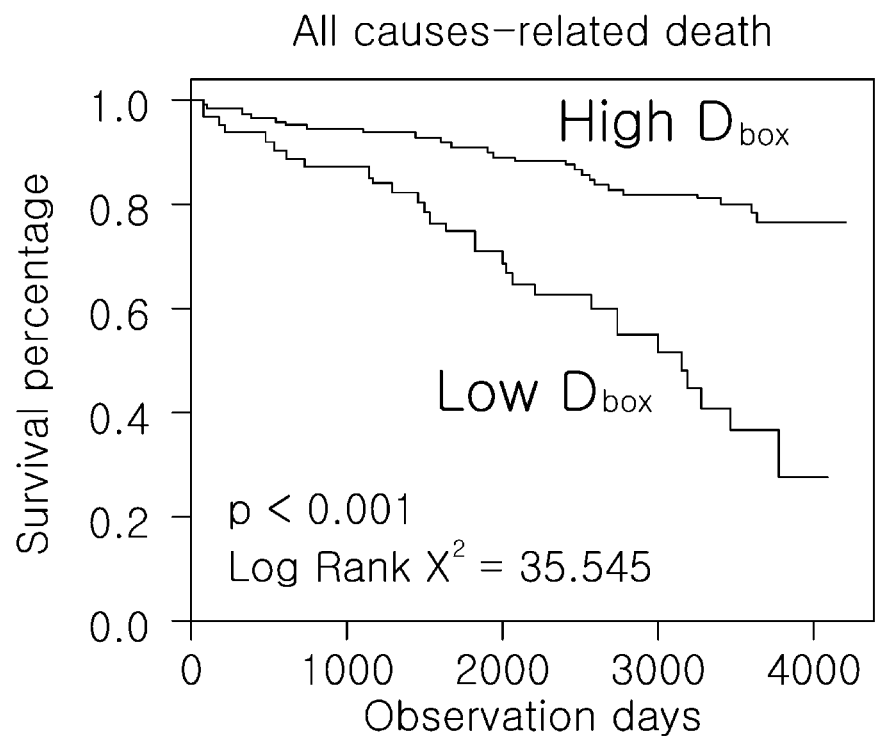
FIGS. 8A and 8B are graphs showing prognosis prediction information according to some embodiments of the present disclosure.
Figure 8B:
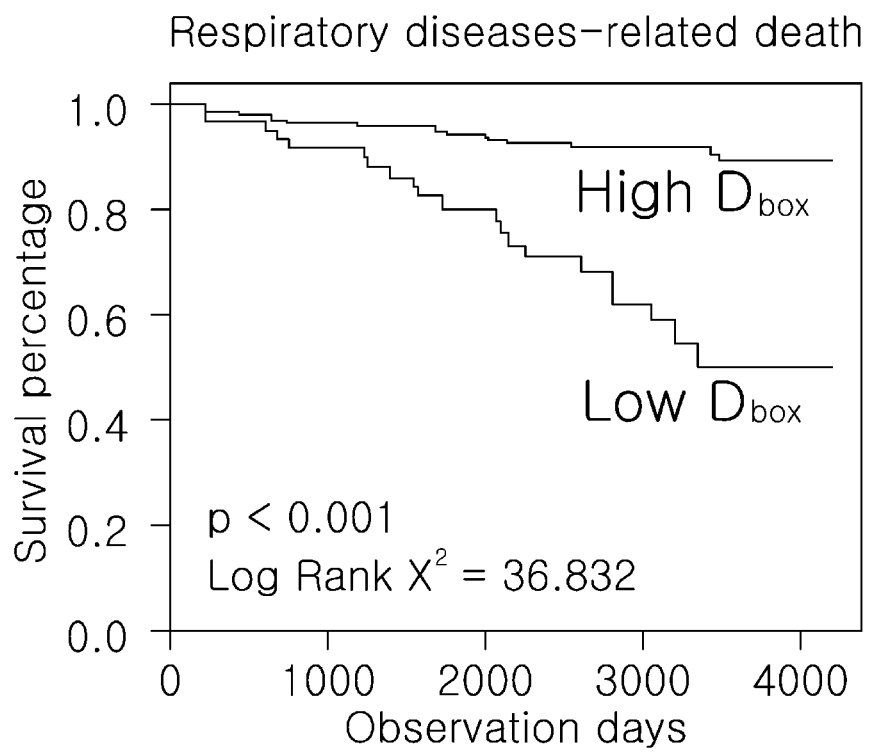

FIGS. 8A and 8B are graphs showing prognosis state prediction information according to according to some embodiments of the present disclosure.

Referring to FIGS. 8A and 8B, graphs to which the box counting scheme as a three-dimensional fractal dimension calculation scheme is applied is shown.

The graphs in FIGS. 8A and 8B are calculated based on pre-collected clinical and image data of a KOLD (Korean Obstructive Lung Disease) cohort (hereinafter, "KOLD cohort").

Specifically, the graphs of FIGS. 8A and 8B are calculated based on (i) a patient with a complete intake-exhalation pair chest CT image in the KOLD image database among patients registered in the KOLD cohort; (ii) a patient with complete demographic/clinical/pulmonary function test data in the KOLD clinical database, among patients registered in the KOLD cohort; (iii) a patient without a history of pulmonary resection, pneumoconiosis, silicosis among patients registered in the KOLD cohort; and (iv) a patient with no evidence of tuberculosis-related lung destruction or bronchiectasis based on chest radiography, among patients registered in the KOLD cohort.

In particular, FIG. 8A is a graph comparing all-causes related death results between patients with high and low fractal dimensions.

FIG. 8B is a graph comparing respiratory disease related death results between patients with high and low fractal dimensions.

A vertical axis of FIG. 8A and FIG. 8B is an index indicating a probability of survival of a patient. A horizontal axis in FIG. 8A and FIG. 8B is an indicator of days for which the patient was observed.

It may be seen that the survival rate of patients with a low fractal dimension is lowered over the observation time in both of FIG. 8A and FIG. 8B.

Regarding the chronic pulmonary disease, in a 'healthy' state, a normal lung tissue is well preserved in a complex and delicate shape. In an 'unhealthy' state, the complex and delicate shape is lost due to the chronic pulmonary disease.

The lung cancer and the chronic pulmonary disease may have opposite phenomena to each other. For the lung cancer, it may be expected that the higher the shape complexity of a lesion area of the lung cancer, the worse the prognosis. To the contrary, it may be expected that the lower the shape complexity of the lesion site, the higher a treatment effect.

The graphs of FIGS. 8A and 8B are graphs measured for patients with chronic pulmonary disease. Therefore, it may be confirmed that the survival probability over time is high based on the respiratory disease related death results between patients with the high fractal dimension and patients with the low fractal dimension.

The deep neural network (DNN) according to some embodiments of the present disclosure means a system or network that builds at least one layer in at least one computer and performs determinations based on a plurality of data. For example, the DNN may be implemented as a set of layers including a convolutional pooling layer, a locally-connected layer, and a fully-connected layer. The convolutional pooling layer or the locally-connected layer may be configured to extract features in an image. The fully-connected layer may determine a correlation between the features of the image. In some embodiments, an overall structure of the DNN may be constructed such that the convolutional pooling layer is connected to the locally-connected layer which in turn is connected to the fully-connected layer. The DNN may include various determination criteria, that is, parameters, and may add new determination criteria, that is, new parameters, via analysis of an input image.

The DNN according to some embodiments of the present disclosure has a structure referred to as a convolutional neural network suitable for prediction of a state change of a lung disease. The DNN has a structure in which a feature extraction layer that autonomously learns a feature with the greatest discriminative power from given image data is integrated with a prediction layer that learns a prediction model to produce the highest prediction performance based on the extracted feature.

The feature extraction layer has a structure in which a convolution layer for applying a plurality of filters to each region of the image to create a feature map, and a pooling layer for pooling feature maps spatially to extract a feature invariant relative to change in a position or a rotation are repeated alternately with each other multiple times. Thus, the feature extraction layer may extract various levels of features from low-level features such as points, lines, and surfaces to complex and meaningful high-level features.

The convolution layer applies a non-linear activation function to a dot product between a filter and a local receptive field for each patch of an input image to obtain the feature map. Compared to other network architectures, a convolutional neural network (CNN) uses a filter having sparse connectivity and shared weights. This connection structure reduces the number of models to be learned, and realizes efficient learning via a backpropagation algorithm, resulting in improved prediction performance.

The pooling layer (or a sub-sampling layer) creates a new feature map by utilizing local information of the feature map obtained from the previous convolution layer. In general, the feature map newly created by the pooling layer is reduced to a smaller size than a size of an original feature map. A typical pooling method includes a max pooling method which selects a maximum value of a corresponding region in the feature map, and an average pooling method which calculates an average of a corresponding region in the feature map. The feature map of the pooling layer is generally less affected by a location of any structure or pattern in the input image than a feature map of the previous layer is. That is, the pooling layer may extract a feature that is more robust to a regional change such as noise or distortion in the input image or the previous feature map. This may play an important role in classification performance. Another role of the pooling layer is to allow a feature of a wider region to be reflected as a layer goes up to a top learning layer in a deep structure. Thus, the features may be created such that as the feature extraction layers are accumulated one on top of another, a lower layer reflects a local feature and a higher layer reflects an abstract feature of an entire image.

In this way, a feature that was finally extracted via repetition of the convolution layer and the pooling layer may be combined with a classification model such as MLP (Multi-Layer Perception) or SVM (Support Vector Machine) in a form of the fully-connected layer and thus may be used for learning and prediction of the classification model.

However, a structure of the DNN according to some embodiments of the present disclosure is not limited thereto. Rather, neural networks of various structures may be employed.

A pulmonary disease prediction system according to some embodiments of the present disclosure generates prognosis prediction information of the second patient based on the prognosis prediction model. The prognosis prediction model is generated by applying a machine learning algorithm to high-dimensional data of at least one first patient. The high-dimensional data is generated by adding the additional information into the fractal dimension value for each region. The fractal dimension value refers to the fractal complexity of the region-based three-dimensional computed tomography image. The three-dimensional computed tomography image is obtained based on the two-dimensional computed tomography image captured based on each body position of the patient.

The lung disease prediction method according to some embodiments of the present disclosure as descried above may be implemented as a program or an application to be executed in combination with a computer as hardware, and may be stored in a storage medium included in the lung disease prediction apparatus.

The program may include codes coded in computer languages such as C, C++, JAVA, and machine language that a processor (CPU) of the computer may read through a device interface thereof, in order for the computer to read the program and execute methods implemented using the program. The code may include a functional code related to a function defining functions required to execute the methods, and an execution procedure-related control code necessary for the processor of the computer to execute the functions in a predetermined procedure. Moreover, the code may further include a memory reference-related code indicating a location (address) of an internal memory of the computer or an external memory thereto in which additional information or media necessary for the processor to execute the functions is stored. Moreover, when the processor of the computer needs to communicate with any other remote computer or server to execute the functions, the code may further include a communication-related code indicating how to communicate with any other remote computer or server using a communication module of the computer, and indicating information or media to be transmitted and received during the communication.

The storage medium means a medium that stores data semi-permanently, rather than a medium for storing data for a short moment, such as a register, a cache, or a memory, and that may be readable by a machine. Specifically, examples of the storage medium may include, but may not be limited to, ROM, RAM, CD-ROM, a magnetic tape, a floppy disk, and an optical data storage device. That is, the program may be stored in various recording media on various servers to which the computer may access or on various recording media on the user's computer. Moreover, the medium may be distributed over a networked computer system so that a computer readable code may be stored in a distributed scheme.

The steps of the method or the algorithm described in connection with an embodiment of the inventive concept may be implemented directly in hardware, a software module executed by hardware, or a combination thereof. The software module may reside on Random Access Memory (RAM), Read Only Memory (ROM), Erasable Programmable ROM (EPROM), Electrically Erasable Programmable ROM (EEPROM), Flash Memory, Hard Disk, a removable disk, CD-ROM, or any form of computer readable recording medium well known in the art.

According to the present disclosure, using the image information may allow the pulmonary disease prognosis prediction at higher accuracy than that when using a conventional indicator.

Moreover, according to some embodiments of the present disclosure, applying the fractal algorithm less affected by various noises that may arise from varying image sizes, varying aspect ratios, etc. may allow the pulmonary disease prognosis prediction at higher accuracy than that when using a conventional indicator.

Moreover, according to some embodiments of the present disclosure, the use of the fractal dimension value may allow the pulmonary disease prognosis prediction at higher accuracy than that when using a conventional indicator.

Moreover, according to some embodiments of the present disclosure, the pulmonary disease prognosis prediction may be realized at higher accuracy than that when using a conventional indicator, without requiring additional examination to the patient or causing a risk.

The effects of the present disclosure are not limited to the effects mentioned above. Other effects not mentioned will be clearly understood by those skilled in the art from the above description.

While the present disclosure has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A method for predicting a pulmonary disease, the method comprising:
   acquiring, by an image matching processor of a pulmonary disease prediction apparatus, a three-dimensional computed tomography (CT) image from two-dimensional CT images, each of which captures a respective body position of a first patient;
   dividing, by a controller of the pulmonary disease prediction apparatus, the three-dimensional CT image into a plurality of regions, to generate region-based three-dimensional CT images configured to be used for fractal analysis;
   calculating, by the controller, a region-based fractal dimension value indicating a fractal complexity of a respective region-based three-dimensional CT image among the generated region-based three-dimensional CT images;
   adding, by the controller, additional information to the calculated region-based fractal dimension value to generate high-dimensional data; and
   generating, by the controller, status information of the first patient based on a complexity of the generated high-dimensional data, wherein the first patient's state indicated by the generated status information depends on the complexity of the generated high-dimensional data and is differentiated according to a type of the disease to be predicted.

2. The method of claim 1, further comprising:
   generating, by the controller, prognosis prediction information of a second patient based on a prognosis prediction model generated by applying a machine learning algorithm to the high-dimensional data.

3. The method of claim 2, wherein the prognosis prediction model is generated by further adding body information of the first patient to the calculated region-based fractal dimension value, and
   wherein the prognosis prediction information of the second patient is generated by further adding, by the controller, body information of the second patient to the prognosis prediction model.

4. The method of claim 2, further comprising:
   providing, by the controller, the prognosis prediction information to a user device.

5. The method of claim 2, further comprising:
   deriving, by the controller, a treatment timing based on the prognosis prediction information; and
   transmitting, by the controller, the derived treatment timing to a user device.

6. The method of claim 2, further comprising:
   deriving, by the controller, a treatment strategy based on the prognosis prediction information; and
   transmitting, by the controller, the derived treatment strategy to a user device.

7. The method of claim 1, wherein the additional information includes at least one of density information of a lung in an inhalation or exhalation state of the first patient, and administration information on whether contrast media has been administered to the first patient, and
   wherein the generating comprises:
   generating, by the controller, the status information of the first patient based on the complexity of the high-dimensional data, which is generated based on the region-based fractal dimension value including the additional information including the at least one of the density information and the administration information.

8. The method of claim 1, wherein the calculating of the fractal dimension value further includes performing, by the controller, linear approximation of the high-dimensional data,
wherein the fractal dimension value is calculated using a box-count scheme.

9. The method of claim 1, wherein the two-dimensional CT images comprises images captured by the pulmonary disease prediction apparatus or images received from an external apparatus.

10. The method of claim 1, where the dividing comprises:
dividing the three-dimensional CT image into the plurality of regions, wherein each region of the divided plurality of regions corresponds to a different scheme for predicting the pulmonary disease; and
generating, by the controller, based on the divided plurality of regions, the region-based three-dimensional CT images configured to be used for fractal analysis.

11. The method of claim 1, wherein the status information indicates a healthy state when the disease to be predicted is a first pulmonary disease and when the complexity is greater than a threshold, and the status information indicates a unhealthy state when the pulmonary disease to be predicted is a second pulmonary disease and when the complexity is greater than the threshold.

12. A pulmonary disease prediction apparatus comprising:
a processor; and
a memory storing at least one instruction executable by the processor,
wherein the at least one instruction is executed by the processor to:
acquire, through an image matching processor of the pulmonary disease prediction apparatus, a three-dimensional computed tomography (CT) image from two-dimensional CT images, each of which captures a respective body position of a first patient;
divide the three-dimensional CT image into a plurality of regions, to generate region-based three-dimensional CT images configured to be used for fractal analysis;
calculate a region-based fractal dimension value indicating a fractal complexity of a respective region-based three-dimensional CT image among the generated region-based three-dimensional CT images;
add additional information to the calculated region-based fractal dimension value to generate high-dimensional data; and
generate status information of the first patient based on the complexity of the generated high-dimensional data, wherein the first patient's state indicated by the generated status information depends on the complexity of the generated high-dimensional data and is differentiated according to a type of the disease to be predicted.

13. A pulmonary disease prediction system comprising:
a controller configured to generate prognosis prediction information of a second patient based on a prognosis prediction model,
wherein the prognosis prediction model is generated by the controller that applies a machine learning algorithm to high-dimensional data of at least one first patient,
wherein the high-dimensional data is generated by the controller that adds additional information into a region-based fractal dimension value,
wherein the region-based fractal dimension value indicates a fractal complexity of a region-based three-dimensional computed tomography (CT) image,
wherein the region-based three-dimensional CT image is generated by the controller that divides a three-dimensional CT image,
wherein the three-dimensional CT image is obtained based on two-dimensional CT images, each of which captures a respective body position of each of the first patient, and
wherein the first patient's state indicated by the generated status information depends on the complexity of the region-based three-dimensional CT image and is differentiated according to a type of the disease to be predicted.

* * * * *